United States Patent
Tamura (10) Patent No.: US 6,539,075 B1
(45) Date of Patent: Mar. 25, 2003

(54) SLIGHT AMOUNT SAMPLE ANALYZING APPARATUS

(75) Inventor: Koichi Tamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/546,765

(22) Filed: Apr. 11, 2000

(30) Foreign Application Priority Data

Apr. 12, 1999 (JP) .......................................... 11-104573

(51) Int. Cl.⁷ .............................................. G01N 23/22
(52) U.S. Cl. .......................................... 378/45; 378/44
(58) Field of Search ........................... 378/45, 44, 51, 378/190

(56) References Cited

U.S. PATENT DOCUMENTS 4,974,244 A * 11/1990 Torrisi et al. ................. 378/45

FOREIGN PATENT DOCUMENTS

JP    403225267 A  * 10/1991

* cited by examiner

*Primary Examiner*—Robert H. Kim
*Assistant Examiner*—Hoon K. Song
(74) *Attorney, Agent, or Firm*—Adams & Wilks

(57) ABSTRACT

An apparatus for preventing scattering of a primary X-ray beam during sample residue measurement using drip and dry analysis on an organic thin film sample support. A primary X-ray beam is transmitted through the organic film, and a hole is formed in a sample stage through which the X-ray passes. The surface of the hole is coated with a heavy metal film, and thereby substantially reduces scattering of the X-ray.

28 Claims, 7 Drawing Sheets

SLIGHT AMOUNT SAMPLE ANALYZING APPARATUS

BACKGROUND OF THE INVENTION

1. Field of the Invention

This invention relates to a fluorescent X-ray analyzing apparatus for conducting element analysis by detecting a secondarily-produced X-ray emanating from a sample in response to illuminating an X-ray onto the sample.

2. Description of the Prior Art

There are broad uses of the fluorescent X-ray analyzing apparatus for conducting element analysis by illuminating a primary X-ray onto a sample and detecting an X-ray secondarily produced from the sample in response thereto.

Particularly, there is a proposal of a method in which, in order to measure an element contained in slight amount contained in a solution, approximately 50 micro-liters of a solution is dripped onto an extremely-thin organic thin film through a micropipette and then dried so that the "residue" on the organic thin film can be thereafter measured by a fluorescent X-ray analyzing apparatus (called an organic thin film drip and dry method) (disclosed in 34th X-ray analysis forum, on Nov. 10, 1998). The principle of this measurement is briefly explained.

Figure 2:
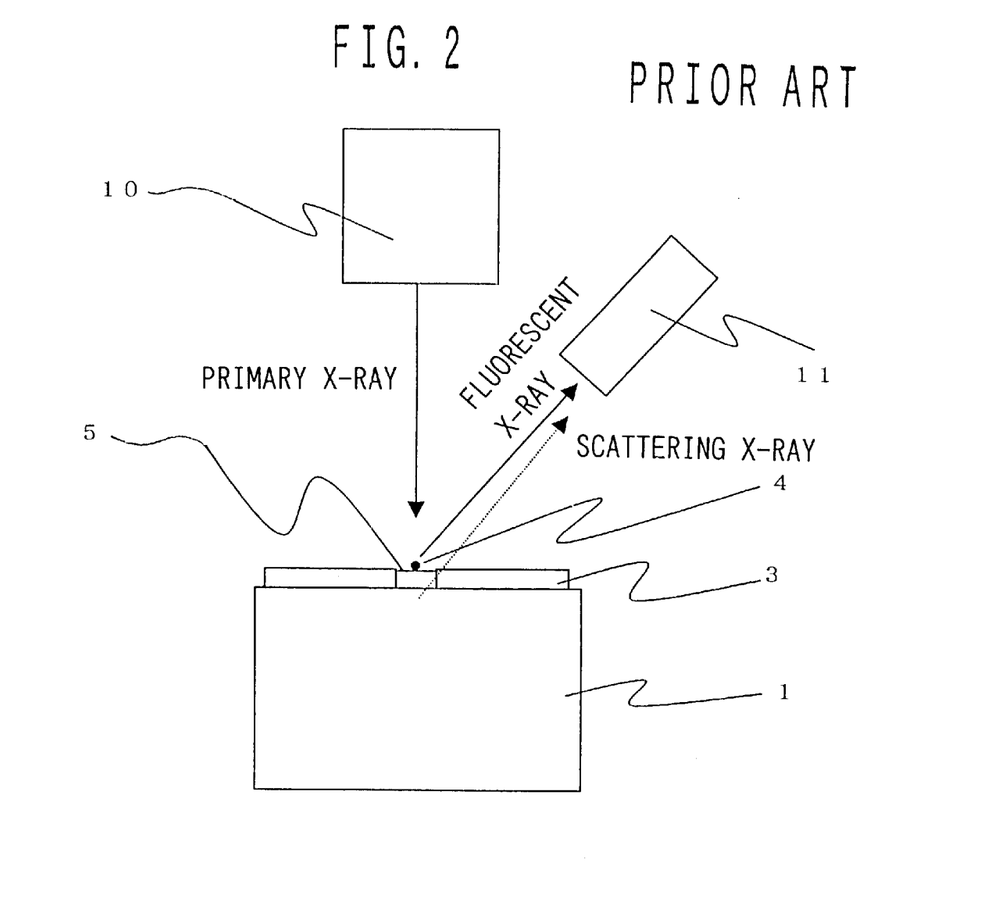
FIG. 2 is a schematic view of a conventional X-ray analyzing apparatus.

Referring to FIG. 2, there is illustrated a schematic view where measurement is conducted with a conventionally-used fluorescent X-ray analyzing apparatus.

Numeral 1 is a sample stage and numeral 3 is an organic thin film support member.

Further, numeral 4 is a residue and numeral 5 is an organic thin film.

Furthermore, numeral 10 is a X-ray source and numeral 11 is a detector.

When illuminating a primary x-ray to a sample, an X-ray spectrum obtained by a detector includes (1) a fluorescent X-ray due to an element contained in the sample and (2) a component of the primary X-ray reaching the detector due to scattering of the primary X-ray (includes diffraction) upon the sample. The scattering X-ray might form a broad background over a wide energy range of the spectrum. In the meanwhile, because the scattering X-ray decreases in intensity with a decrease in sample thickness, it is possible to obtain a spectrum with a low background.

The relationship between a detection lower limit and a background intensity can be defined as follows:

(X-ray intensity obtained from element concentration at detection lower limit)=$3 \times \sqrt{}$ (background X-ray intensity).

Accordingly, the use of the organic thin film dip-and-dry method greatly improves a lower limit of detection as compared to the method of analysis that directly illuminates an X-ray to a solution sample.

In the meanwhile, in the fluorescent X-ray analyzing apparatus for measuring an organic thin film formed through dripping and drying a sample, a top-radiation system for illuminating a primary X-ray from the sample above is adopted so as not to spill a residue out of the organic thin film. Meanwhile, a fluorescent X-ray analysis apparatus is used to illuminate a primary X-ray only to an area of the residue. This apparatus is provided with a collimator for forming a beam as fine as about 1 to 2 mm, a sample stage for positioning a the residue, and a sample observation mechanism.

In the conventional apparatus, however, the sample stage is made of a resin or aluminum. Accordingly, when a primary X-ray is illuminated on to an organic thin film, the X-ray transmitting through the organic thin film impinges upon the sample stage. This results in a problem that the detector detect a scattering X-ray from the stage and a fluorescent X-ray thus causing a background.

SUMMARY OF THE INVENTION

In order to solve the problem, in the present invention, a hole is formed in a sample stage which has a greater diameter than that of a beam of a primary X-ray and a coating film is formed of a heavy metal on the bottom and inner surfaces of the hole. The sample stage is made lightweight to have a movement mechanism, and uses resin or light metal such as aluminum. Because the intensity of a scattering X-ray is inversely proportional to a mean atomic number of an object, the scattering X-ray from the sample stage formed of resin or light metal is extremely high in intensity. To form the entire sample stage of a heavy metal is not advantageous because of a resulting increase in weight. Accordingly, the sample stage itself is formed of a resin or a lightweight material, and a hole is formed in a position so that a primary X-ray is caused to pass therethrough. The hole at its bottom surface where the primary X-ray is to be finally stopped is made of a heavy metal. Due to this, the scattering X-ray is reduced in intensity without requiring weight increase for the entire stage. Furthermore, a heavy metal coating film is also formed on an inner surface of the hole, thereby preventing scattering at the inner surface. Meanwhile, the scattering X-ray from the heavy metal coating film, although low in intensity, possibly cause an interference peak on a spectrum. However, in the case that the coating film is formed of the same substance as an element of a target material of the X-ray tube, an effect is obtained in that the interference peak will not increase because of the fact that a characteristic X-ray peak concerning the target material element exists in nature on the spectrum.

DETAILED DESCRIPTION OF THE PREFERRED EMBODIMENTS

Preferred embodiments of the present invention will now be described with reference to the drawings.

Figure 1:
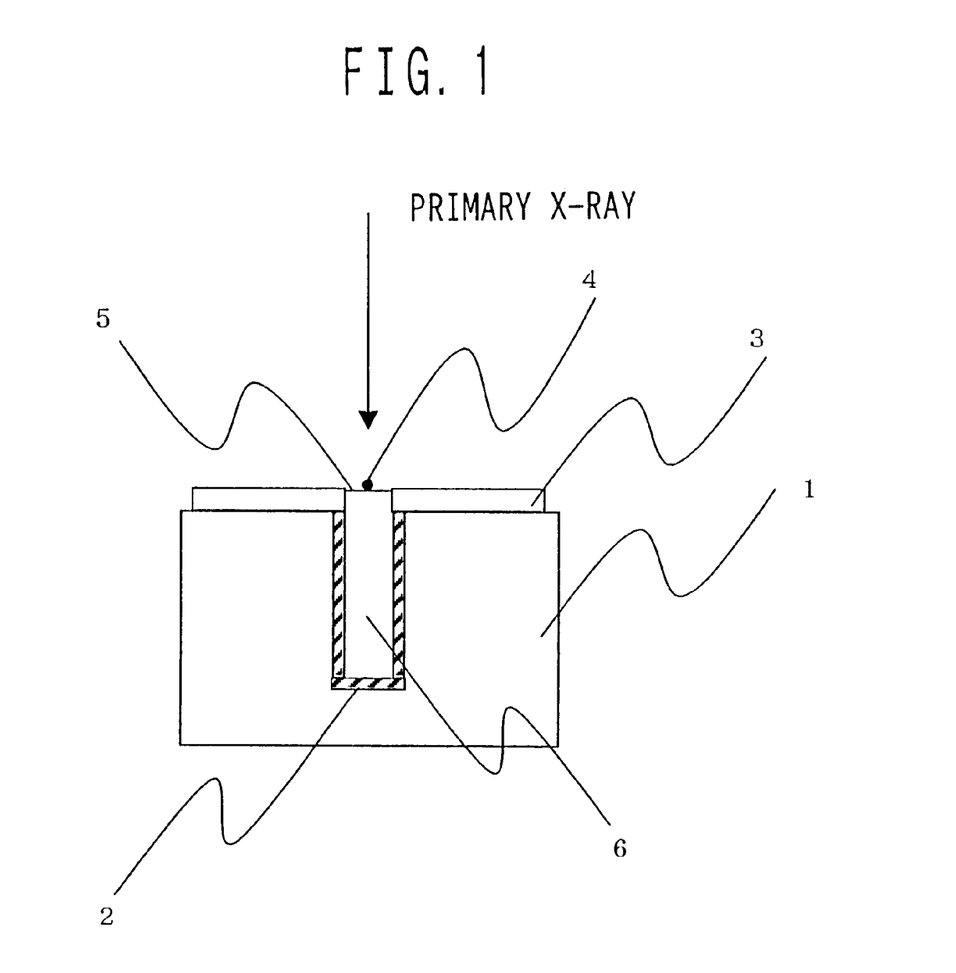
FIG. 1 is a sectional view of a sample stage of an X-ray analyzing apparatus according to the present invention.

Referring to FIG. 1, there is illustrated a sectional view of a sample stage of an X-ray analysis apparatus to be used in the present invention. An organic thin film 5 has a thickness of approximately several hundreds of nanometers. This organic thin film is formed and supported in an opening having a diameter of approximately 5–6 mm formed in a resin formed organic thin film support member 3 with a thickness of 1–2 mm. A residue 4 is formed with a diameter of 1–2 mm by dripping and drying a solution sample.

A movable sample stage 1 on which the organic thin film support member 3 is placed is formed of a resin or light metal for weight reduction. In the sample stage, a hole 6 is formed in a circular cylindrical form having a greater diameter than the diameter of the residue or in a squared cylinder form circumscribing the circular cylinder. The hole 6 at its bottom and inner surfaces is formed with a heavy metal coating film 2. The heavy metal may comprise lead or tungsten or the like. Alternatively, it may comprise the same substance used as an element for an X-ray tube target material for the purpose of not increasing unwanted interference peaks on an obtained spectrum. The film forming method may use metal plating, plating evaporation or the like. The film should be formed with a sufficient thickness such that a primary X-ray is fully attenuated does not reach a base of the sample stage. Furthermore, it is further effective for background reduction to form the hole to such a depth that an X-ray radiation spot formed in the hole bottom surface by the primary X-ray cannot be seen from a detector.

The hole 6 has a diameter or a side length in the range of 2 mm to 10 mm.

A measurer puts the organic thin film support member 3 on the sample stage 1 such that the residue 4 is positioned in a center of the hole 6. Measurement is made by moving the sample stage 1 onto illuminate a primary X-ray to the residue 4.

Figure 3:
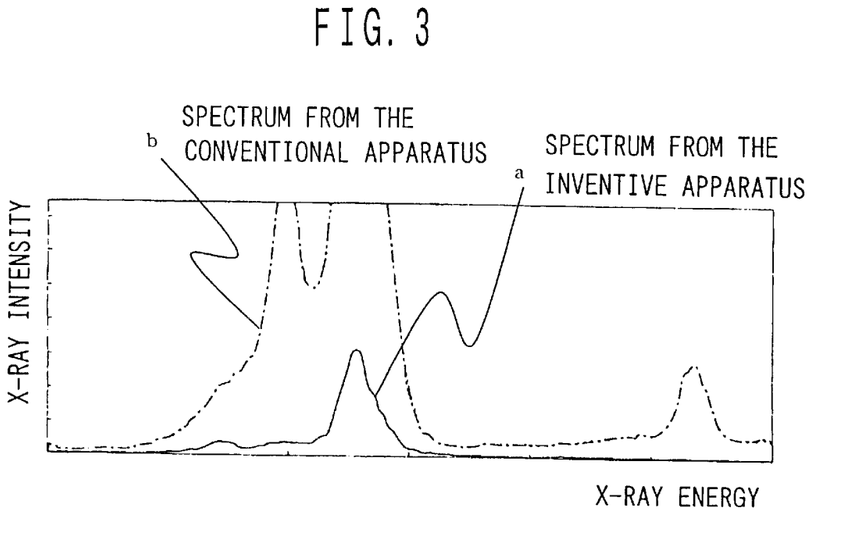
FIG. 3 is a figure showing a comparison between an X-ray spectrum obtained in the X-ray analyzing apparatus of the invention and an X-ray spectrum obtained in the conventional apparatus.

Referring to FIG. 3, there is illustrated an X-ray spectrum when measuring a slight amount of metal in a solution according to the invention, wherein curve (a) is a spectrum obtained in the fluorescent X-ray analyzing apparatus of the invention while curve (b) is a spectrum obtained by resting an organic thin film support member as it is on the conventional resin stage. It is clearly understood that the invention provides a spectrum lower in background.

Figure 4:
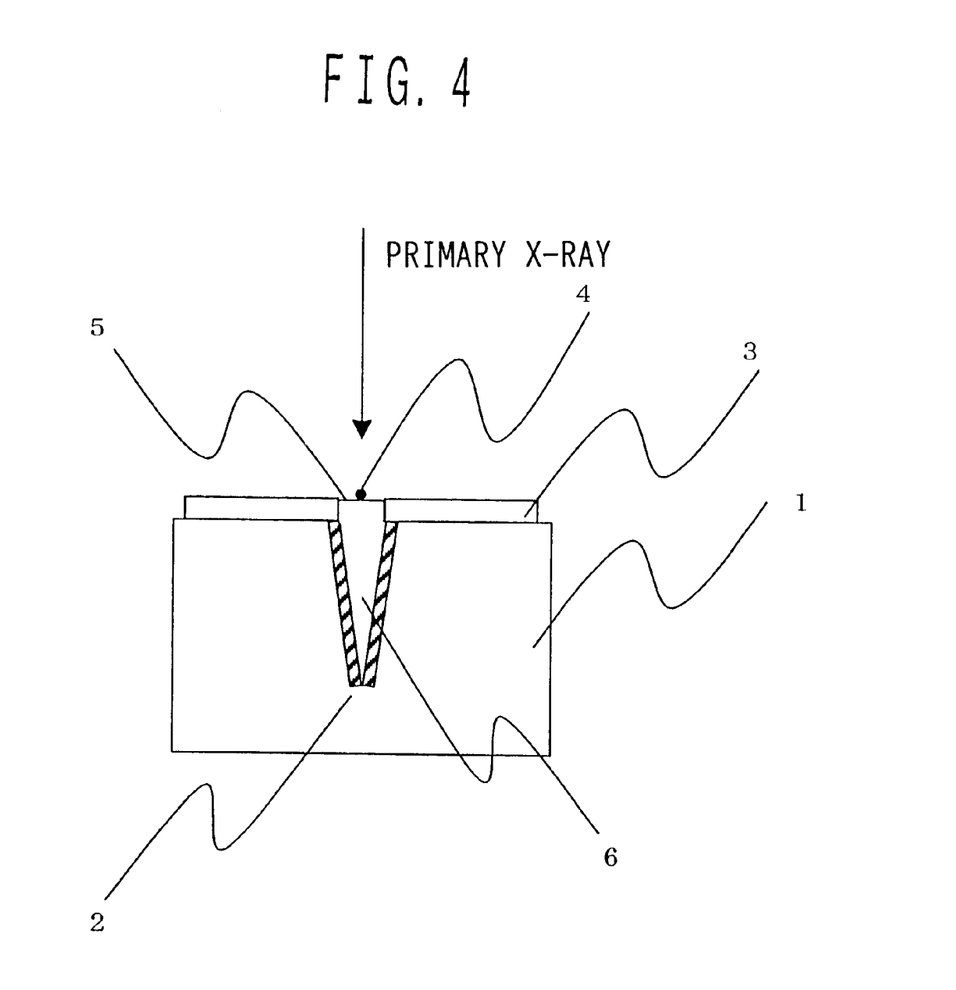
FIG. 4 is a sectional view of a sample stage showing a second embodiment of an X-ray analyzing apparatus of the invention.

Referring to FIG. 4, there is shown a second embodiment of a sample stage of an X-ray analyzing apparatus to be used in the invention. In the second embodiment a hole 6 formed in a stage 1 is in a circular cone shape having as a bottom surface a circle with a greater diameter than a diameter of a residue or in a squared cone circumscribing that.

Figure 5:
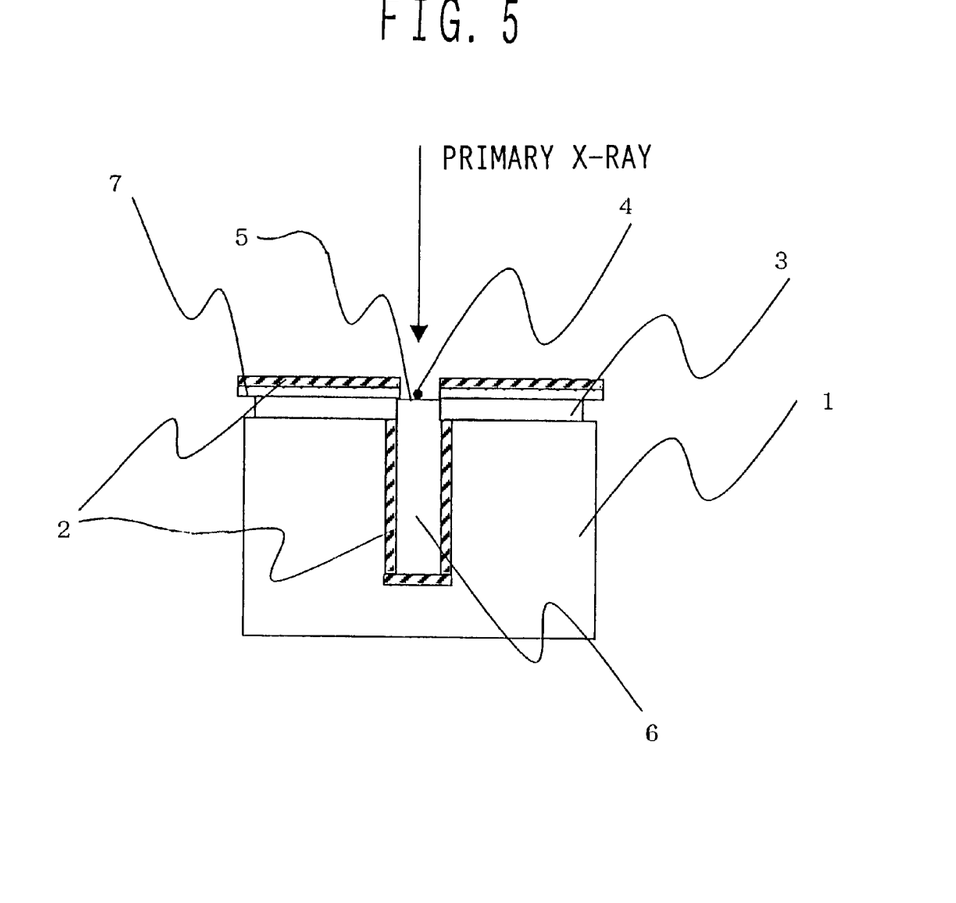
FIG. 5 is a sectional view of a sample stage showing a third embodiment of an X-ray analyzing apparatus of the invention.

Referring to FIG. 5, there is illustrated a third embodiment of a sample stage of an X-ray analyzing apparatus to be used in the invention. This embodiment has a structure that a lid 7 having a hole 6 with a same size as a hole 6 can be placed on an organic thin film support member 3, wherein the lid has upon the upper face the same coating film as is formed in the bottom and inner surfaces of the hole 6 in the first embodiment. Due to this, a primary X-ray is illuminated to and scattered upon the bottom of the hole 6 to cause an X-ray. The X-ray is further scattered by a structural member, such as a collimator or shutter in the apparatus. This is scattered by the organic thin film support member 3 usually formed of resin or the like and incident on the detector, providing an effect to prevent against forming background.

Figure 6:
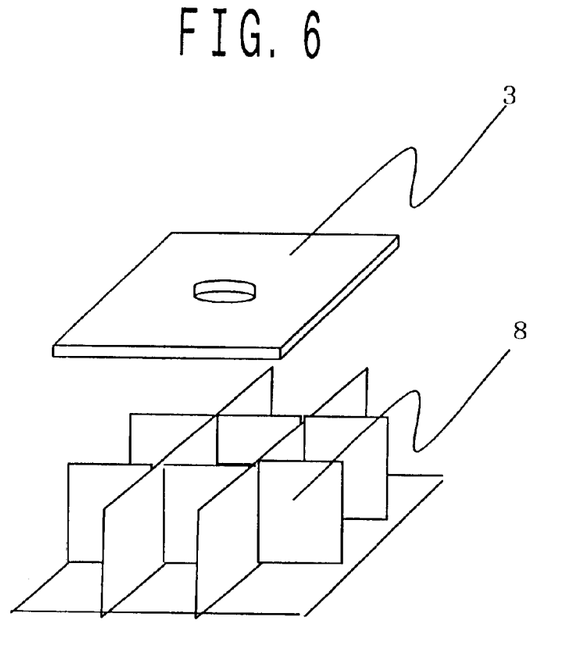
FIG. 6 is a sectional view of a sample stage showing a fourth embodiment of an X-ray analyzing apparatus of the invention.

Referring to FIG. 6, there is illustrated a fourth embodiment of a sample stage of an X-ray analyzing apparatus to be used in the invention. This embodiment uses two lengthwise and breadthwise heavy metal plates 8 that are combined in a grid form in place of the heavy metal coat film formed in the inner surface of the hole 6 in the first embodiment. In place of the coat film in the bottom surface of the hole 6, one heavy metal plate is used.

Figure 7:
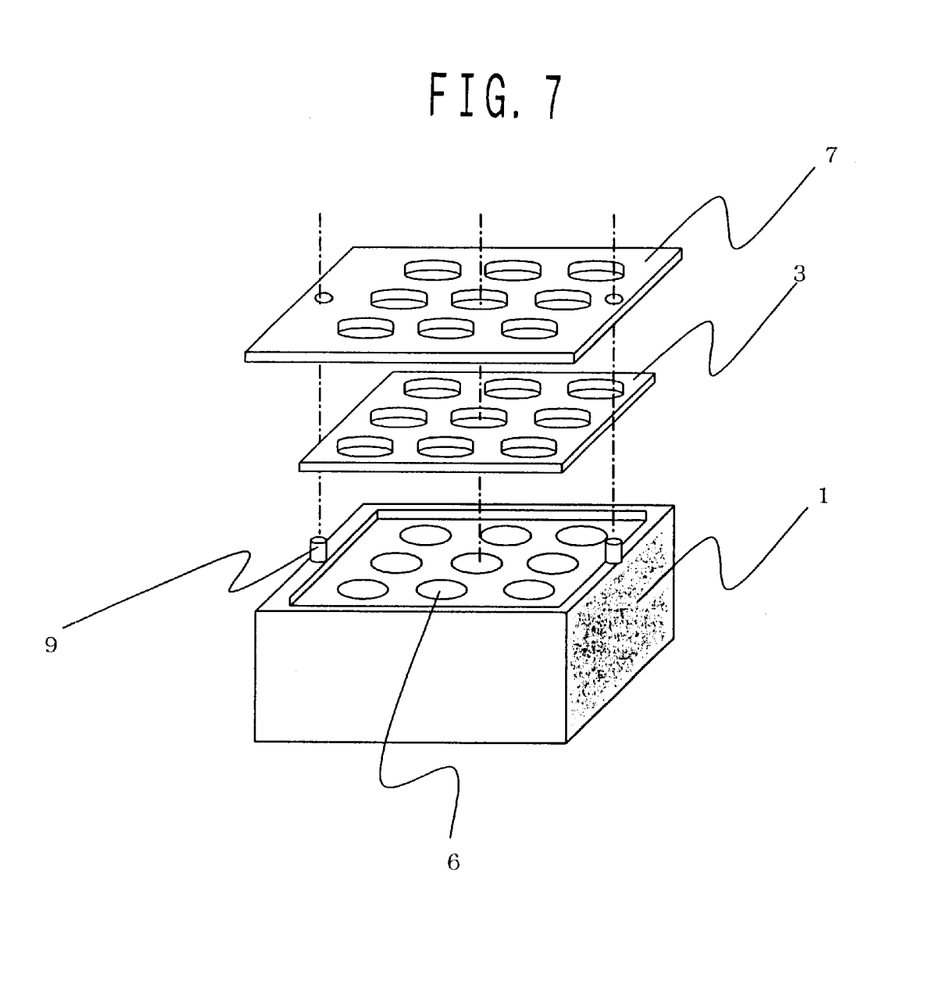
FIG. 7 is a sectional view of a sample stage showing a fifth embodiment of an X-ray analyzing apparatus of the invention.

Referring to FIG. 7, there is illustrated a fifth embodiment of a sample stage of an X-ray analyzing apparatus to be used in the invention. A sample stage 1 is formed with a step so that an organic thin film support member 3 can be well fitted therein. The sample stage is formed with a plurality of circular cylinder holes 6 having respective centers in position aligned with opening centers of the organic thin film support member 3 formed by a plurality of organic thin films 5. Each hole 6 has inner and bottom surfaces formed with a heavy metal coat film. Further, a lid 7 is formed a heavy metal coat film upon the upper face the same coat film, a lid 7 is opened with fitting holes so that positioning pins 9 formed standing on the sample stage 1 can be fitted therewith. The lid has holes opened in same positions as the holes 6 of the sample stage as viewed from above when fitted. Due to this, the measurer can conduct analysis on a plurality of samples by merely moving the sample stage 1 without labor and time of positional adjustment between the sample stage 1, the organic thin film support member 3 and the lid 7.

As described above, in an fluorescent X-ray analyzing apparatus for performing element analysis by detecting an X-ray secondarily produced from a sample when illuminating an X-ray to the sample, particularly a fluorescent X-ray analyzing apparatus for analyzing a residue formed by dripping and drying a solution sample on an extremely thin organic film, a hole is formed in the sample stage and a heavy metal coat film is applied on an inner and bottom surfaces of the hole. Accordingly, it is possible to reduce the intensity of a scattering X-ray caused due to scattering of a primary X-ray passed through the organic thin film upon the sample stage, and hence a background to be formed due to incidence of the same on a detector.

Also, if the heavy metal coat film uses a same element as a target material of an X-ray tube, an effect is obtained that such an unnecessary fluorescent X-ray peak is caused as might increase the possibility of confusing with a fluorescent X-ray peak due to the sample.

Furthermore, a lid may be used that has on a top surface a same heavy metal coat film as those on the inner and bottom surfaces of the sample stage and can be placed on a support member for the extremely thin organic film rested on the sample stage wherein the lid as viewed from above is opened with a hole in a same position as the sample stage when placed on. This provides an effect that a primary X-ray transmitted through the organic thin film is scattered on the sample stage to cause a scattering X-ray to be scattered by a structure inside an apparatus and further scattered on the organic thin film support member resulting in incidence on the detector and hence forming a background.

What is claimed is:

1. An apparatus for analyzing a slight amount of a sample, comprising:
   an X-ray source for producing a primary X-ray beam;
   a movable sample stage for supporting a sample onto which the primary X-ray beam is to be illuminated; and
   a detector for detecting a fluorescent X-ray produced by the sample in response to illumination by the primary X-ray beam; and
   a lid for placement on a measurement sample disposed on the sample stage;
   wherein the sample stage has one or more holes formed therein each having a central axis on an axis of the primary X-ray beam during use and being in the form of one of a circular cylinder having a diameter within the range of approximately 2 mm-to 10 mm or a squared cylinder having a side length within the range of approximately 2 mm to 10 mm, and each hole having a coating film formed of a heavy metal covering an inner surface thereof; and wherein the lid has a heavy metal coating film formed of the same heavy metal as that covering the inner surface of the hole of the sample stage and a hole having a diameter within a range of approximately 2 mm to 10 mm so as to expose a hole formed in the sample stage when the lid is laid on the sample stage.

2. An apparatus for analyzing a slight amount of a sample, comprising:

an X-ray source for producing a primary X-ray beam;

a movable sample stage for supporting a sample onto which the primary X-ray beam is to be illuminated; and a detector for detecting a fluorescent X-ray produced by the sample in response to illumination by the primary X-ray beam; and a lid for placement on a measurement sample disposed on the sample stage;

wherein the sample stage has one more holes formed therein each having a central axis on an axis of the primary X-ray beam during use and being in the form of one of a circular cylinder having a diameter within the range of approximately 2 mm to 10 mm or a squared cylinder having a side length within the range of approximately 2 mm to 10 mm, each hole having a depth set so that an illumination spot formed by the primary X-ray beam on a bottom surface of the hole is not detected by the detector and a coating film formed of a heavy metal covering an inner surface thereof; and wherein the lid has a heavy metal coating film formed of the same heavy metal as that covering the inner surface of the hole of the sample stage, the lid having a hole having a diameter within a range of approximately 2 mm to 10 mm so as to expose a hole formed in the sample stage when the lid is laid on the sample stage.

3. An apparatus for analyzing a slight amount of a sample, comprising:

an X-ray source for producing a primary X-ray beam;

a movable sample stage for supporting a sample onto which the primary X-ray beam is to be illuminated; and a detector for detecting a fluorescent X-ray produced by the sample in response to illumination by the primary X-ray beam;

wherein the sample stage is formed of a plastic or light metal and has one or more holes formed therein, each hole having a central axis on an axis of the primary X-ray beam during use and being in the form of one of an inverted cone having a diameter within the range of approximately 2 mm to 10 mm at an opening thereof and gradually decreasing in a direction of irradiation of the primary X-ray beam or of a squared inverted cone having a side length at an opening thereof within the range of approximately 2 mm to 10 mm, and each hole having a coating film formed of a heavy metal covering an inner surface thereof.

4. An apparatus for analyzing a slight amount of a sample, comprising:

an X-ray source for producing a primary X-ray beam;

a movable sample stage for supporting a sample onto which the primary X-ray beam is to be illuminated; and a detector for detecting a fluorescent X-ray produced by the sample in response to illumination by the primary X-ray beam;

wherein the sample stage is comprises a grid formed of a plurality of first flat plates arranged in parallel with an axis of the primary X-ray beam so that the plates form a plurality of adjacent rectangular openings, and adjacent parallel plates are spaced from each other at an interval within the range of approximately 2 mm to 10 mm a second flat plate forming a bottom surface supporting the first plates;

wherein the first and second slates are formed of a material having a heavy metal surface, and a height of the first plates is set such that plates, if considered as a hole, has such a depth that an illumination spot of the primary X-ray beam formed on the bottom surface cannot be detected by the detector.

5. An apparatus for analyzing a slight amount of a sample according to claim 4; further comprising a lid for placement on a measurement sample disposed on the sample stage and having a heavy metal coating film formed of the same heavy metal as that of the grid forming the sample stage, the lid having a hole having a diameter within the range of approximately 2 mm to 10 mm so as to expose a hole formed in said sample stage when the lid is laid on the sample stage.

6. An apparatus for analyzing a slight amount of a sample according to any one of claims 1 to 4 and 6; wherein the coating film is formed of the same material as a target element of the X-ray source.

7. An apparatus for analyzing a slight amount of a sample according to claim 1; further comprising a positioning member comprising one of a step or a pin formed on the sample stage for positioning the lid with respect to the sample stage such that each hole formed in the sample stage coincides with each hole formed in the lid when the lid is placed on the sample stage.

8. An apparatus for analyzing a slight amount of a sample according to claim 6; further comprising a positioning member comprising one of a step or a pin formed on the sample stage for positioning the lid with respect to the sample stage such that the rectangular openings formed in the grid coincide with each hole formed in the lid when the lid is placed on the sample stage.

9. An apparatus for analyzing a slight amount of a sample according to claim 8; further comprising a sample holder comprised of a support member having an opening therethrough and an organic thin film formed on the support member to cover the opening, the sample being formed on the organic thin film over the opening by dripping a solution of the sample and drying the solution; wherein the sample stage has a stepped portion for fitting the sample holder.

10. An apparatus for analyzing a slight amount of a sample, comprising:

a sample holder comprised of a support member having an opening therethrough and an organic thin film formed on the support member to cover the opening, the sample comprising a dried residue of a sample solution dripped onto the organic thin film over the opening;

an X-ray source for producing a primary X-ray beam;

a sample stage for supporting a sample onto which the primary X-ray beam is to be illuminated; and a detector for detecting a fluorescent X-ray emanating from the sample in response to illumination of the sample by the primary X-ray beam;

wherein the sample stage has one or more holes formed therein over which a sample is to be disposed during measurement so that the primary X-ray beam passes into the hole, each hole having a surface formed of a heavy metal which is the same heavy metal used as a target element of the X-ray source.

11. An apparatus for analyzing a slight amount of a sample according to claim 10; wherein the holes are in the form of a circular cylinder having a diameter within the range of approximately 2 mm to 10 mm.

12. An apparatus for analyzing a slight amount of a sample according to claim 10; wherein the holes are in the form of a squared cylinder having a side length within the range of approximately 2 mm to 10 mm.

13. An apparatus for analyzing a slight amount of a sample according to claim 10; wherein the holes have a coating film formed of a heavy metal covering an inner surface thereof.

14. An apparatus for analyzing a slight amount of a sample according to claim 10; wherein the holes have depth set so that an illumination spot formed by the primary X-ray beam on a bottom surface thereof is not detected by the detector.

15. An apparatus for analyzing a slight amount of a sample according to claim 10; wherein the sample stage is formed of a plurality of first flat plates arranged parallel to one another and a plurality of second flat plates arranged parallel to one another and intersecting the first plates to form a grid structure.

16. An apparatus for analyzing a slight amount of a sample according to claim 15; wherein adjacent ones of the first flat plates are spaced from each other by an amount within the range of approximately 2 mm to 10 mm.

17. An apparatus for analyzing a slight amount of a sample according to claim 16; wherein adjacent ones of the second flat plates are spaced from each other by an amount within the range of approximately 2 mm to 10 mm.

18. An apparatus for analyzing a slight amount of a sample according to claim 15; further comprising a lid for placement on a measurement sample disposed on the sample stage and having a heavy metal surface formed of the same heavy metal as that of the grid structure forming the sample stage, the lid having a hole having a diameter within the range of approximately 2 mm to 10 mm so as to expose a hole formed in said sample stage when the lid is in position on the sample stage.

19. An apparatus for analyzing a slight amount of a sample according to claim 10; further comprising a lid for placement over a measurement sample disposed on the sample stage and having a heavy metal surface formed of the same heavy metal as that covering the inner surface of the hole of the sample stage, the lid having a hole having a diameter within a range of approximately 2 mm to 10 mm so as to expose a hole formed in the sample stage when the lid is in position on the sample stage.

20. An apparatus for analyzing a slight amount of a sample according to claim 10; wherein the heavy metal of the hole surface is same material as that of a target element of the X-ray source.

21. An apparatus for analyzing a slight amount of a sample according to claim 1; further comprising a sample holder comprising a support member having an opening therethrough and an organic thin film formed on the support member to cover the opening, the sample comprising a dried residue of a sample solution dripped onto the organic thin film over the opening.

22. An apparatus for analyzing a slight amount of a sample according to claim 1; wherein the squared cylinder comprises a polygon cylinder which circumscribes the circular cylinder.

23. An apparatus for analyzing a slight amount of a sample according to claim 2; further comprising a sample holder comprising a support member having an opening therethrough and an organic thin film formed on the support member to cover the opening, the sample comprising a dried residue of a sample solution dripped onto the organic thin film over the opening.

24. An apparatus for analyzing a slight amount of a sample according to claim 2; wherein the squared cylinder comprises a polygon cylinder which circumscribes the circular cylinder.

25. An apparatus for analyzing a slight amount of a sample according to claim 3; further comprising a sample holder comprising a support member having an opening therethrough and an organic thin film formed on the support member to cover the opening, the sample comprising a dried residue of a sample solution dripped onto the organic thin film over the opening.

26. An apparatus for analyzing a slight amount of a sample according to claim 3; wherein the squared cylinder comprises a polygon cylinder which circumscribes the circular cylinder.

27. An apparatus for analyzing a slight amount of a sample according to claim 4; further comprising a sample holder comprising a support member having an opening therethrough and an organic thin film formed on the support member to cover the opening, the sample comprising a dried residue of a sample solution dripped onto the organic thin film over the opening.

28. An apparatus for analyzing a slight amount of a sample according to claim 4; wherein the squared cylinder comprises a polygon cylinder which circumscribes the circular cylinder.

* * * * *